United States Patent
Ma et al.

(10) Patent No.: US 11,341,633 B2
(45) Date of Patent: May 24, 2022

(54) SYSTEMS AND METHODS FOR ADAPTIVE ENHANCEMENT OF VASCULAR IMAGING

(71) Applicant: Edan Instruments, Inc., Guangdong (CN)

(72) Inventors: Jinghui Ma, Shenzhen (CN); Seshadri Srinivasan, Sunnyvale, CA (US); Feng Ling, Shenzhen (CN)

(73) Assignee: EDAN INSTRUMENTS, INC., Shenzhen (CN)

( * ) Notice: Subject to any disclaimer, the term of this patent is extended or adjusted under 35 U.S.C. 154(b) by 367 days.

(21) Appl. No.: 16/617,425

(22) PCT Filed: May 31, 2017

(86) PCT No.: PCT/CN2017/086542
§ 371 (c)(1),
(2) Date: Nov. 26, 2019

(87) PCT Pub. No.: WO2018/218479
PCT Pub. Date: Dec. 6, 2018

(65) Prior Publication Data
US 2020/0151872 A1    May 14, 2020

(51) Int. Cl.
*G06K 9/00* (2022.01)
*A61B 8/00* (2006.01)
(Continued)

(52) U.S. Cl.
CPC ............ *G06T 7/0012* (2013.01); *A61B 8/085* (2013.01); *A61B 8/4427* (2013.01); *A61B 8/488* (2013.01);
(Continued)

(58) Field of Classification Search
USPC ................ 382/100, 103, 106, 128–133, 154, 382/172–173, 181, 189, 199, 254, 274,
(Continued)

(56) References Cited

U.S. PATENT DOCUMENTS

| | | | |
|---|---|---|---|
| 8,047,989 B2* | 11/2011 | Oshiki | A61B 8/469 600/437 |
| 2011/0033098 A1* | 2/2011 | Richter | G06T 7/33 382/131 |

(Continued)

FOREIGN PATENT DOCUMENTS

| | | |
|---|---|---|
| CN | 1921802 A | 2/2007 |
| CN | 101210966 A | 7/2008 |

(Continued)

OTHER PUBLICATIONS

International Search Report and Written Opinion issued in International Patent Application No. PCT/CN2017/086542, dated Feb. 12, 2018.

*Primary Examiner* — Seyed H Azarian

(57) ABSTRACT

An ultrasound system (100) includes an ultrasound transducer, a processing circuit (210, 300), and a display. The ultrasound transducer is configured to detect ultrasound information regarding a patient and output the ultrasound information as an ultrasound data sample. The processing circuit (210, 300) is configured to segment the ultrasound data sample into a binary image including at least one first region and at least one second region, obtain a first location of a first vascular feature of the binary image based on a boundary between the at least one first region and the at least one second region, and modify the binary image based on the first location of the first vascular feature. The first vascular feature is associated with an intima media thickness. The display is configured to display the modified image.

18 Claims, 5 Drawing Sheets

(51) Int. Cl.
*G06T 7/00* (2017.01)
*G06T 7/136* (2017.01)
*G06T 7/12* (2017.01)
*G06T 7/155* (2017.01)
*A61B 8/08* (2006.01)
*G06T 11/00* (2006.01)

(52) U.S. Cl.
CPC ............... *G06T 7/12* (2017.01); *G06T 7/136* (2017.01); *G06T 7/155* (2017.01); *G06T 11/001* (2013.01); *G06T 2207/10132* (2013.01); *G06T 2207/30104* (2013.01)

(58) Field of Classification Search
USPC ............. 382/276, 291, 305, 321; 378/4, 21; 600/443, 437
See application file for complete search history.

(56) References Cited

U.S. PATENT DOCUMENTS

| | | | |
|---|---|---|---|
| 2011/0299754 A1* | 12/2011 | Suri | A61B 5/02007 382/131 |
| 2012/0316442 A1* | 12/2012 | Suri | G06T 7/11 600/443 |
| 2014/0355858 A1* | 12/2014 | O'Dell | G06T 7/11 382/131 |
| 2016/0104292 A1* | 4/2016 | Srinivasan | G06V 10/40 382/131 |
| 2018/0005372 A1* | 1/2018 | Wang | G06K 9/44 |

FOREIGN PATENT DOCUMENTS

| | | |
|---|---|---|
| CN | 102188262 A | 9/2011 |
| CN | 104665872 A | 6/2015 |
| CN | 105380682 A | 3/2016 |

* cited by examiner

SYSTEMS AND METHODS FOR ADAPTIVE ENHANCEMENT OF VASCULAR IMAGING

TECHNICAL FIELD

The present disclosure generally relates to ultrasound systems. In some implementations, the present disclosure relates to ultrasound systems that adaptively enhance vascular imaging using intima media thickness.

BACKGROUND

Ultrasound systems can be used to detect information regarding a patient, including information regarding blood flow in a patient, in order to display such information to a medical professional or other user so that the user can make medical decisions based on the information. For example, an ultrasound transducer can transmit ultrasound waves into a body of the patient and detect return waves that may have been modified by blood flow and vascular structures of the body of the patient, and a computer can communicate with the ultrasound transducer to receive ultrasound information from the ultrasound transducer and display spectra and/or images using the ultrasound information. However, various factors involved in the process of detecting and displaying ultrasound information may make it difficult to distinguish vascular features from blood flow, which can reduce the signal to noise ratio of the information ultimately provided to the user. As such, it may be difficult to display such information in an accurate and easily understood manner and thus difficult for the user to make medical decisions based on the information.

SUMMARY

One embodiment relates to a system. The system includes an ultrasound transducer, a processing circuit, and a display. The ultrasound transducer is configured to detect ultrasound information regarding a patient and output the ultrasound information as an ultrasound data sample. The processing circuit is configured to segment the ultrasound data sample into a binary image including at least one first region and at least one second region, obtain a first location of a first vascular feature of the binary image based on a boundary between the at least one first region and the at least one second region, and modify the binary image based on the first location of the first vascular feature. The display is configured to display the modified image.

Another embodiment relates to a system. The system includes a processing circuit. The processing circuit is configured to receive an ultrasound data sample from an ultrasound transducer. The ultrasound data sample represents an anatomy of a patient. The processing circuit is configured to segment the ultrasound data sample into a binary image including at least one first region and at least one second region. The processing circuit is configured to obtain a first location of a first vascular feature of the binary image based on a boundary between the at least one first region and the at least one second region. The processing circuit is configured to modify the binary image based on the first location of the first vascular feature.

Another embodiment relates to a method. The method includes receiving an ultrasound data sample associated with ultrasound information regarding a patient. The method includes segmenting the ultrasound data sample into a binary image including at least one first region and at least one second region. The method includes obtaining a first location of a first vascular feature of the binary image based on a boundary between the at least one first region and the at least one second region. The method includes modifying the binary image based on the first location of the first vascular feature. The method includes displaying the modified image.

DETAILED DESCRIPTION

Before turning to the Figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Referring to the Figures generally, a system can include an ultrasound transducer, a processing circuit, and a display. The ultrasound transducer is configured to detect ultrasound information regarding a patient and output the ultrasound information as an ultrasound data sample. The processing circuit is configured to segment the ultrasound data sample into a binary image including at least one first region and at least one second region. The processing circuit is configured to obtain a first location of a first vascular feature of the binary image based on a boundary between the at least one first region and the at least one second region. The processing circuit is configured to modify the binary image based on the first location of the first vascular feature. The display is configured to display the modified image. In some embodiments, the processing circuit is configured to segment the ultrasound data sample based on a brightness threshold. In some embodiments, the processing circuit is configured to obtain locations of vascular features including a media-adventitia line and a lumen-intima line.

By modifying the binary image based on the location of one or more vascular features, the visualization experience and medical diagnosis operation using the ultrasound system is improved, such as by identifying vascular features such as intima-media thickness in real time, enhancing contrast between vessel walls and blood flow to more accurately and precisely display ultrasound information, identifying vascular anatomy for subsequent use in initializing ultrasound display parameters, differentiating veins from arteries in vascular imaging, suppressing bleed in color Doppler imaging, and/or suppressing clutter within the lumen where blood flow is displayed.

A. Ultrasound System

Figure 1A:
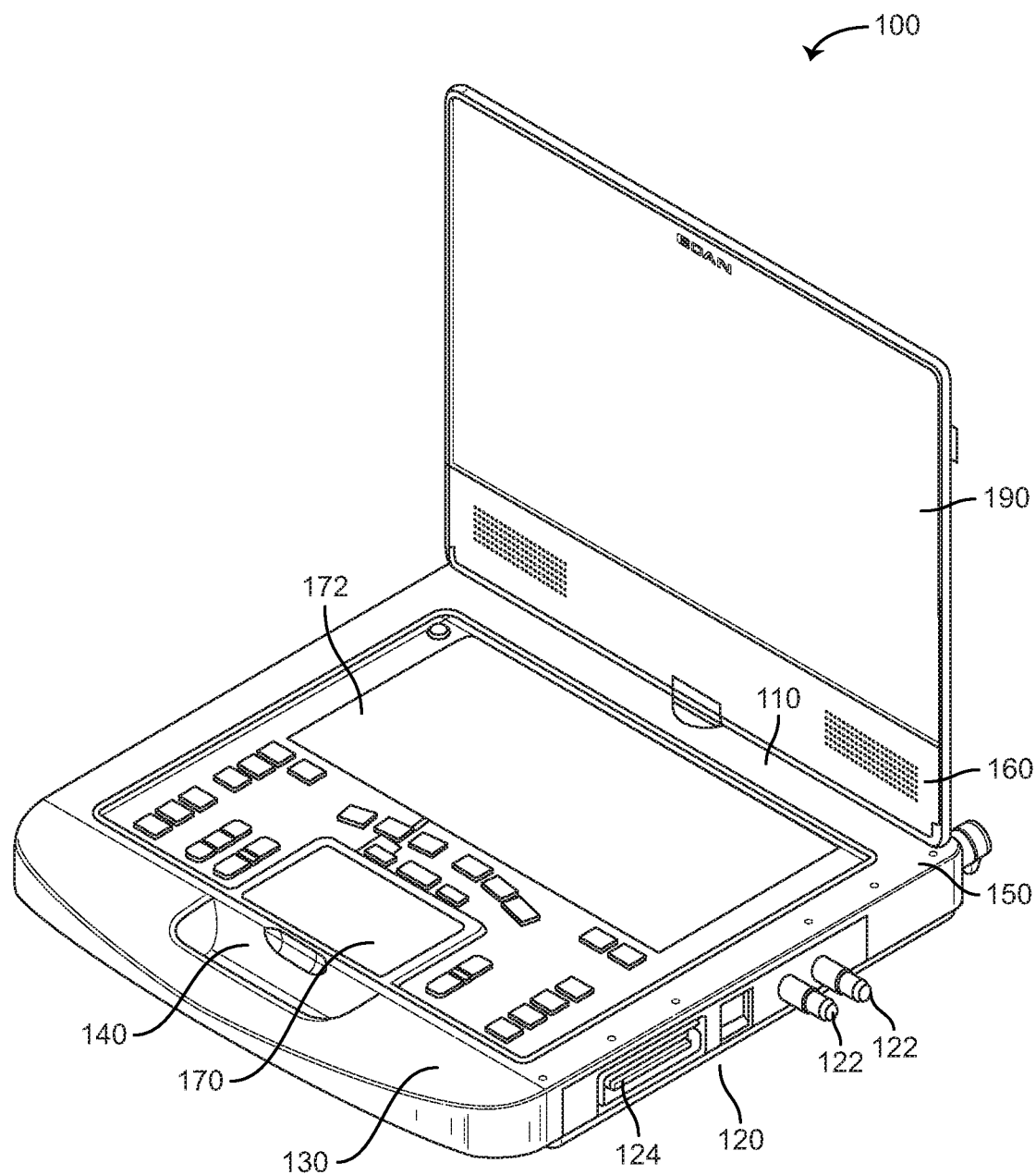
FIG. 1A is a perspective view of an ultrasound system according to an illustrative embodiment.

Referring now to FIG. 1A, one embodiment of portable ultrasound system 100 is illustrated. Portable ultrasound system 100 may include display support system 110 for increasing the durability of the display system. Portable ultrasound system 100 may further include locking lever system 120 for securing ultrasound probes and/or transducers. Some embodiments of portable ultrasound system 100 include ergonomic handle system 130 for increasing portability and usability. Further embodiments include status indicator system 140 which displays, to a user, information relevant to portable ultrasound system 100. Portable ultrasound system 100 may further include features such as an easy to operate and customizable user interface, adjustable feet, a backup battery, modular construction, cooling systems, etc.

Still referring to FIG. 1A, main housing 150 houses components of portable ultrasound system 100. In some embodiments, the components housed within main housing 150 include locking lever system 120, ergonomic handle system 130, and status indicator system 140. Main housing 150 may also be configured to support electronics modules which may be replaced and/or upgraded due to the modular construction of portable ultrasound system 100. In some embodiments, portable ultrasound system 100 includes display housing 160. Display housing 160 may include display support system 110. In some embodiments, portable ultrasound system 100 includes touchpad 170 for receiving user inputs and displaying information, touchscreen 172 for receiving user inputs and displaying information, and main screen 190 for displaying information.

Figure 1B:
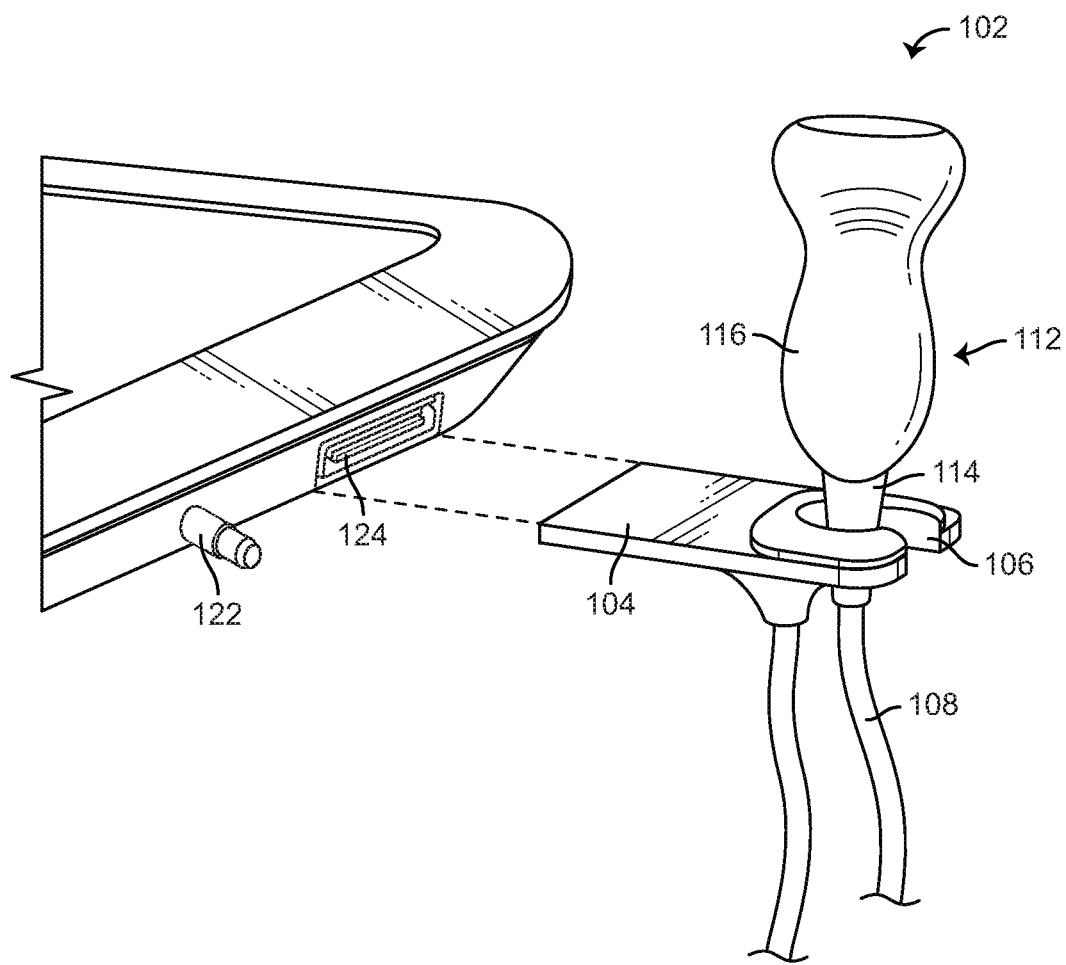
FIG. 1B is a perspective view of components of an ultrasound system according to an illustrative embodiment.

Referring now to FIG. 1B, ultrasound transducer assembly 102 is shown. According to an exemplary embodiment, ultrasound transducer assembly 102 includes a connection assembly to pin (122) or socket (124) type ultrasound interface, shown as ultrasound interface connector 104, coupled to cable 108. Cable 108 may be coupled to a transducer probe 112. While FIG. 1B shows only one transducer assembly 102, more transducer assemblies may be coupled to the ultrasound system 100 based on the quantity of pin (122) or socket (124) type ultrasound interfaces.

Ultrasound interface connector 104 is movable between a removed position with respect to pin (122) or socket (124) type ultrasound interface, in which ultrasound interface connector 104 is not received by pin (122) or socket (124) type ultrasound interface, a partially connected position, in which ultrasound interface connector 104 is partially received by pin (122) or socket (124) type ultrasound interface, and a fully engaged position, in which ultrasound interface connector 104 is fully received by pin (122) or socket (124) type ultrasound interface in a manner that electrically couples transducer probe 112 to ultrasound system 100. In an exemplary embodiment, pin (122) or socket (124) type ultrasound interface may include a sensor or switch that detects the presence of the ultrasound interface connector 104.

In various exemplary embodiments contained herein, the ultrasound interface connector 104 may house passive or active electronic circuits for affecting the performance of the connected transducers. For example, in some embodiments the transducer assembly 102 may include filtering circuitry, processing circuitry, amplifiers, transformers, capacitors, batteries, failsafe circuits, or other electronics which may customize or facilitate the performance of the transducer and/or the overall ultrasound machine. In an exemplary embodiment, ultrasound interface connector 104 may include a bracket 106, where the transducer probe 112 may be stored when not in use.

Transducer probe 112 transmits and receives ultrasound signals that interact with the patient during the diagnostic ultrasound examination. The transducer probe 112 includes a first end 114 and a second end 116. The first end 114 of the transducer probe 112 may be coupled to cable 108. The first end 114 of the transducer probe 112 may vary in shape to properly facilitate the cable 108 and the second end 116. The second end 116 of the transducer probe 112 may vary in shape and size to facilitate the conduction of different types of ultrasound examinations. These first end 114 and second end 116 of transducer probe 112 variations may allow for better examination methods (e.g., contact, position, location, etc.).

A user (e.g., a sonographer, an ultrasound technologist, etc.) may remove a transducer probe 112 from a bracket 106 located on ultrasound interface connector 104, position transducer probe 112, and interact with main screen 190 to conduct the diagnostic ultrasound examination. Conducting the diagnostic ultrasound examination may include pressing transducer probe 112 against the patient's body or placing a variation of transducer probe 112 into the patient. The ultrasound spectrum or image acquired may be viewed on the main screen 190.

Figure 2:
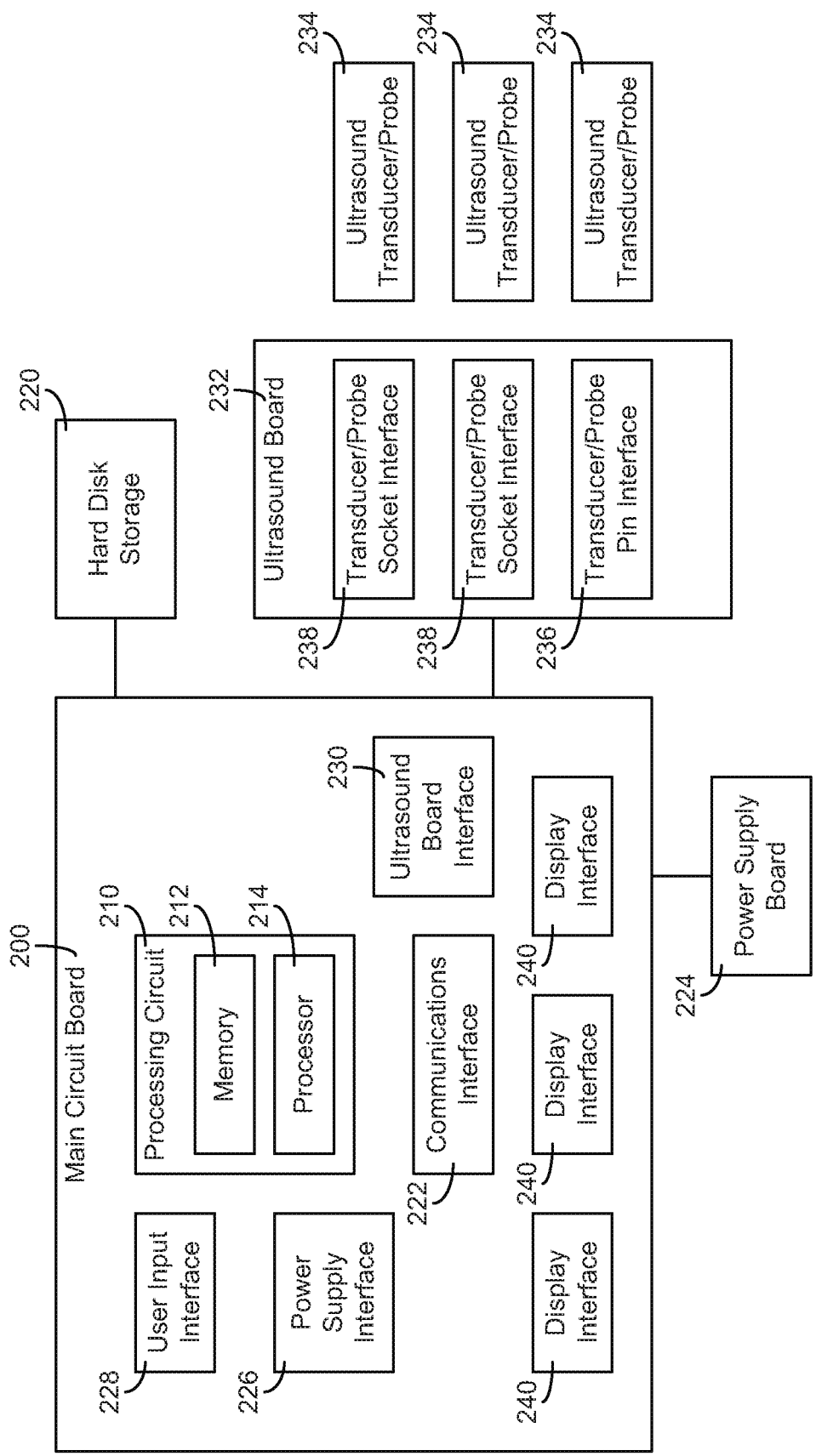
FIG. 2 is a block diagram illustrating components of an ultrasound system according to an illustrative embodiment.

Referring to FIG. 2, a block diagram shows internal components of one embodiment of portable ultrasound system 100. Portable ultrasound system 100 includes main circuit board 200. Main circuit board 200 carries out computing tasks to support the functions of portable ultrasound system 100 and provides connection and communication between various components of portable ultrasound system 100. In some embodiments, main circuit board 200 is configured so as to be a replaceable and/or upgradable module.

To perform computational, control, and/or communication tasks, main circuit board 200 includes processing circuit 210. Processing circuit 210 is configured to perform general processing and to perform processing and computational tasks associated with specific functions of portable ultrasound system 100. For example, processing circuit 210 may perform calculations and/or operations related to producing a spectrum and/or an image from signals and/or data provided by ultrasound equipment, running an operating system for portable ultrasound system 100, receiving user inputs, etc. Processing circuit 210 may include memory 212 and processor 214 for use in processing tasks. For example, processing circuit 210 may perform calculations and/or operations.

Processor 214 may be, or may include, one or more microprocessors, application specific integrated circuits (ASICs), circuits containing one or more processing components, a group of distributed processing components, circuitry for supporting a microprocessor, or other hardware configured for processing. Processor 214 is configured to execute computer code. The computer code may be stored in memory 212 to complete and facilitate the activities described herein with respect to portable ultrasound system 100. In other embodiments, the computer code may be retrieved and provided to processor 214 from hard disk storage 220 or communications interface 222 (e.g., the computer code may be provided from a source external to main circuit board 200).

Memory 212 may be any volatile or non-volatile computer-readable storage medium capable of storing data or computer code relating to the activities described herein. For example, memory 212 may include modules which are computer code modules (e.g., executable code, object code, source code, script code, machine code, etc.) configured for execution by processor 214. Memory 212 may include computer code engines or circuits that can be similar to the computer code modules configured for execution by processor 214. Memory 212 may include computer executable code related to functions including ultrasound imagining, battery management, handling user inputs, displaying data, transmitting and receiving data using a wireless communication device, etc. In some embodiments, processing circuit 210 may represent a collection of multiple processing devices (e.g., multiple processors, etc.). In such cases, processor 214 represents the collective processors of the devices and memory 212 represents the collective storage devices of the devices. When executed by processor 214, processing circuit 210 is configured to complete the activities described herein as associated with portable ultrasound system 100, such as for generating ultrasound spectra and/or images (e.g., for display by touchscreen 172 and/or display 190) based on segmenting ultrasound information and obtaining locations of vascular features.

Hard disk storage 220 may be a part of memory 212 and/or used for non-volatile long term storage in portable ultrasound system 100. Hard disk storage 220 may store local files, temporary files, ultrasound spectra and/or images, patient data, an operating system, executable code, and any other data for supporting the activities of portable ultrasound device 100 described herein. In some embodiments, hard disk storage 220 is embedded on main circuit board 200. In other embodiments, hard disk storage 220 is located remote from main circuit board 200 and coupled thereto to allow for the transfer of data, electrical power, and/or control signals. Hard disk storage 220 may be an optical drive, magnetic drive, a solid state hard drive, flash memory, etc.

In some embodiments, main circuit board 200 includes communications interface 222. Communications interface 222 may include connections which enable communication between components of main circuit board 200 and communications hardware. For example, communications interface 222 may provide a connection between main circuit board 200 and a network device (e.g., a network card, a wireless transmitter/receiver, etc.). In further embodiments, communications interface 222 may include additional circuitry to support the functionality of attached communications hardware or to facilitate the transfer of data between communications hardware and main circuit board 200. In other embodiments, communications interface 222 may be a system on a chip (SOC) or other integrated system which allows for transmission of data and reception of data. In such a case, communications interface 222 may be coupled directly to main circuit board 200 as either a removable package or embedded package.

Some embodiments of portable ultrasound system 100 include power supply board 224. Power supply board 224 includes components and circuitry for delivering power to components and devices within and/or attached to portable ultrasound system 100. In some embodiments, power supply board 224 includes components for alternating current and direct current conversion, for transforming voltage, for delivering a steady power supply, etc. These components may include transformers, capacitors, modulators, etc. to perform the above functions. In further embodiments, power supply board 224 includes circuitry for determining the available power of a battery power source. In other embodiments, power supply board 224 may receive information regarding the available power of a battery power source from circuitry located remote from power supply board 224. For example, this circuitry may be included within a battery. In some embodiments, power supply board 224 includes circuitry for switching between power sources. For example, power supply board 224 may draw power from a backup battery while a main battery is switched. In further embodiments, power supply board 224 includes circuitry to operate as an uninterruptable power supply in conjunction with a backup battery. Power supply board 224 also includes a connection to main circuit board 200. This connection may allow power supply board 224 to send and receive information from main circuit board 200. For example, power supply board 224 may send information to main circuit board 200 allowing for the determination of remaining battery power. The connection to main circuit board 200 may also allow main circuit board 200 to send commands to power supply board 224. For example, main circuit board 200 may send a command to power supply board 224 to switch from one source of power to another (e.g., to switch to a backup battery while a main battery is switched). In some embodiments, power supply board 224 is configured to be a module. In such cases, power supply board 224 may be configured so as to be a replaceable and/or upgradable module. In some embodiments, power supply board 224 is or includes a power supply unit. The power supply unit may convert AC power to DC power for use in portable ultrasound system 100. The power supply may perform additional functions such as short circuit protection, overload protection, undervoltage protection, etc. The power supply may conform to ATX specification. In other embodiments, one or more of the above described functions may be carried out by main circuit board 200.

Main circuit board 200 may also include power supply interface 226 which facilitates the above described communication between power supply board 224 and main circuit board 200. Power supply interface 226 may include connections which enable communication between components of main circuit board 200 and power supply board 224. In further embodiments, power supply interface 226 includes additional circuitry to support the functionality of power supply board 224. For example, power supply interface 226 may include circuitry to facilitate the calculation of remaining battery power, manage switching between available power sources, etc. In other embodiments, the above described functions of power supply board 224 may be carried out by power supply interface 226. For example, power supply interface 226 may be a SOC or other integrated system. In such a case, power supply interface 226 may be coupled directly to main circuit board 200 as either a removable package or embedded package.

With continued reference to FIG. 2, some embodiments of main circuit board 200 include user input interface 228. User input interface 228 may include connections which enable communication between components of main circuit board 200 and user input device hardware. For example, user input interface 228 may provide a connection between main circuit board 200 and a capacitive touchscreen, resistive touchscreen, mouse, keyboard, buttons, and/or a controller for the proceeding. In one embodiment, user input interface 228 couples controllers for touchpad 170, touchscreen 172, and main screen 190 to main circuit board 200. In other embodiments, user input interface 228 includes controller circuitry for touchpad 170, touchscreen 172, and main screen 190. In some embodiments, main circuit board 200 includes a plurality of user input interfaces 228. For example, each user input interface 228 may be associated with a single input device (e.g., touchpad 170, touchscreen 172, a keyboard, buttons, etc.).

In further embodiments, user input interface 228 may include additional circuitry to support the functionality of attached user input hardware or to facilitate the transfer of data between user input hardware and main circuit board 200. For example, user input interface 228 may include controller circuitry so as to function as a touchscreen controller. User input interface 228 may also include circuitry for controlling haptic feedback devices associated with user input hardware. In other embodiments, user input interface 228 may be a SOC or other integrated system which allows for receiving user inputs or otherwise controlling user input hardware. In such a case, user input interface 228 may be coupled directly to main circuit board 200 as either a removable package or embedded package.

Main circuit board 200 may also include ultrasound board interface 230 which facilitates communication between ultrasound board 232 and main circuit board 200. Ultrasound board interface 230 may include connections which enable communication between components of main circuit board 200 and ultrasound board 232. In further embodiments, ultrasound board interface 230 includes additional circuitry to support the functionality of ultrasound board 232. For example, ultrasound board interface 230 may include circuitry to facilitate the calculation of parameters used in generating a spectrum and/or an image from ultrasound data provided by ultrasound board 232. In some embodiments, ultrasound board interface 230 is a SOC or other integrated system. In such a case, ultrasound board interface 230 may be coupled directly to main circuit board 200 as either a removable package or embedded package.

In other embodiments, ultrasound board interface 230 includes connections which facilitate use of a modular ultrasound board 232. Ultrasound board 232 may be a module (e.g., ultrasound module) capable of performing functions related to ultrasound imaging (e.g., multiplexing sensor signals from an ultrasound probe/transducer, controlling the frequency of ultrasonic waves produced by an ultrasound probe/transducer, etc.). The connections of ultrasound board interface 230 may facilitate replacement of ultrasound board 232 (e.g., to replace ultrasound board 232 with an upgraded board or a board for a different application). For example, ultrasound board interface 230 may include connections which assist in accurately aligning ultrasound board 232 and/or reducing the likelihood of damage to ultrasound board 232 during removal and/or attachment (e.g., by reducing the force required to connect and/or remove the board, by assisting, with a mechanical advantage, the connection and/or removal of the board, etc.).

In embodiments of portable ultrasound system 100 including ultrasound board 232, ultrasound board 232 includes components and circuitry for supporting ultrasound imaging functions of portable ultrasound system 100. In some embodiments, ultrasound board 232 includes integrated circuits, processors, and memory. Ultrasound board 232 may also include one or more transducer/probe socket interfaces 238. Transducer/probe socket interface 238 enables ultrasound transducer/probe 234 (e.g., a probe with a socket type connector) to interface with ultrasound board 232. For example, transducer/probe socket interface 238 may include circuitry and/or hardware connecting ultrasound transducer/probe 234 to ultrasound board 232 for the transfer of electrical power and/or data. Transducer/probe socket interface 238 may include hardware which locks ultrasound transducer/probe 234 into place (e.g., a slot which accepts a pin on ultrasound transducer/probe 234 when ultrasound transducer/probe 234 is rotated). In some embodiments, ultrasound board 232 includes two transducer/probe socket interfaces 238 to allow the connection of two socket type ultrasound transducers/probes 187.

In some embodiments, ultrasound board 232 also includes one or more transducer/probe pin interfaces 236. Transducer/probe pin interface 236 enables an ultrasound transducer/probe 234 with a pin type connector to interface with ultrasound board 232. Transducer/probe pin interface 236 may include circuitry and/or hardware connecting ultrasound transducer/probe 234 to ultrasound board 232 for the transfer of electrical power and/or data. Transducer/probe pin interface 236 may include hardware which locks ultrasound transducer/probe 234 into place. In some embodiments, ultrasound transducer/probe 234 is locked into place with locking lever system 120. In some embodiments, ultrasound board 232 includes more than one transducer/probe pin interfaces 236 to allow the connection of two or more pin type ultrasound transducers/probes 234. In such cases, portable ultrasound system 100 may include one or more locking lever systems 120. In further embodiments, ultrasound board 232 may include interfaces for additional types of transducer/probe connections.

With continued reference to FIG. 2, some embodiments of main circuit board 200 include display interface 240. Display interface 240 may include connections which enable communication between components of main circuit board 200 and display device hardware. For example, display interface 240 may provide a connection between main circuit board 200 and a liquid crystal display, a plasma display, a cathode ray tube display, a light emitting diode display, and/or a display controller or graphics processing unit for the proceeding or other types of display hardware. In some embodiments, the connection of display hardware to main circuit board 200 by display interface 240 allows a processor or dedicated graphics processing unit on main circuit board 200 to control and/or send data to display hardware. Display interface 240 may be configured to send display data to display device hardware in order to produce a spectrum and/or an image. In some embodiments, main circuit board 200 includes multiple display interfaces 240 for multiple display devices (e.g., three display interfaces 240 connect three displays to main circuit board 200). In other embodiments, one display interface 240 may connect and/or support multiple displays. In one embodiment, three display interfaces 240 couple touchpad 170, touchscreen 172, and main screen 190 to main circuit board 200.

In further embodiments, display interface 240 may include additional circuitry to support the functionality of attached display hardware or to facilitate the transfer of data between display hardware and main circuit board 200. For example, display interface 240 may include controller circuitry, a graphics processing unit, video display controller, etc. In some embodiments, display interface 240 may be a SOC or other integrated system which allows for displaying spectra and/or images with display hardware or otherwise controlling display hardware. Display interface 240 may be coupled directly to main circuit board 200 as either a removable package or embedded package. Processing circuit 210 in conjunction with one or more display interfaces 240 may display spectra and/or images on one or more of touchpad 170, touchscreen 172, and main screen 190.

Referring back to FIG. 1A, in some embodiments, portable ultrasound system 100 includes one or more pin type ultrasound probe interfaces 122. Pin type ultrasound interface 122 may allow an ultrasound probe to connect to an ultrasound board 232 included in ultrasound system 100. For example, an ultrasound probe connected to pin type ultrasound interface 122 may be connected to ultrasound board 232 via transducer/probe pin interface 236. In some embodiments, pin type ultrasound interface 122 allows communication between components of portable ultrasound system 100 and an ultrasound probe. For example, control signals may be provided to the ultrasound probe 112 (e.g., controlling the ultrasound emissions of the probe) and data may be received by ultrasound system 100 from the probe (e.g., imaging data).

In some embodiments, ultrasound system 100 may include locking lever system 120 for securing an ultrasound probe. For example, an ultrasound probe may be secured in pin type ultrasound probe interface 122 by locking lever system 120.

In further embodiments, ultrasound system 100 includes one or more socket type ultrasound probe interfaces 124. Socket type ultrasound probe interfaces 124 may allow a socket type ultrasound probe to connect to an ultrasound board 232 included in ultrasound system 100. For example, an ultrasound probe connected to socket type ultrasound probe interface 124 may be connected to ultrasound board 232 via transducer/probe socket interface 238. In some embodiments, socket type ultrasound probe interface 124 allows communication between components of portable ultrasound system 100 and other components included in or connected with portable ultrasound system 100. For example, control signals may be provided to an ultrasound probe (e.g., controlling the ultrasound emissions of the probe) and data may be received by ultrasound system 100 from the probe (e.g., imaging data).

In various embodiments, various ultrasound imaging systems may be provided with some or all of the features of the portable ultrasound system illustrated in FIGS. 1A-1B and -2. In various embodiments, various ultrasound imaging systems may be provided as a portable ultrasound system, a portable ultrasound transducer, a hand-held ultrasound device, a cart-based ultrasound system, an ultrasound system integrated into other diagnostic systems, etc.

B. Systems and Methods for Adaptive Enhancement of Vascular Imaging

Figure 3:
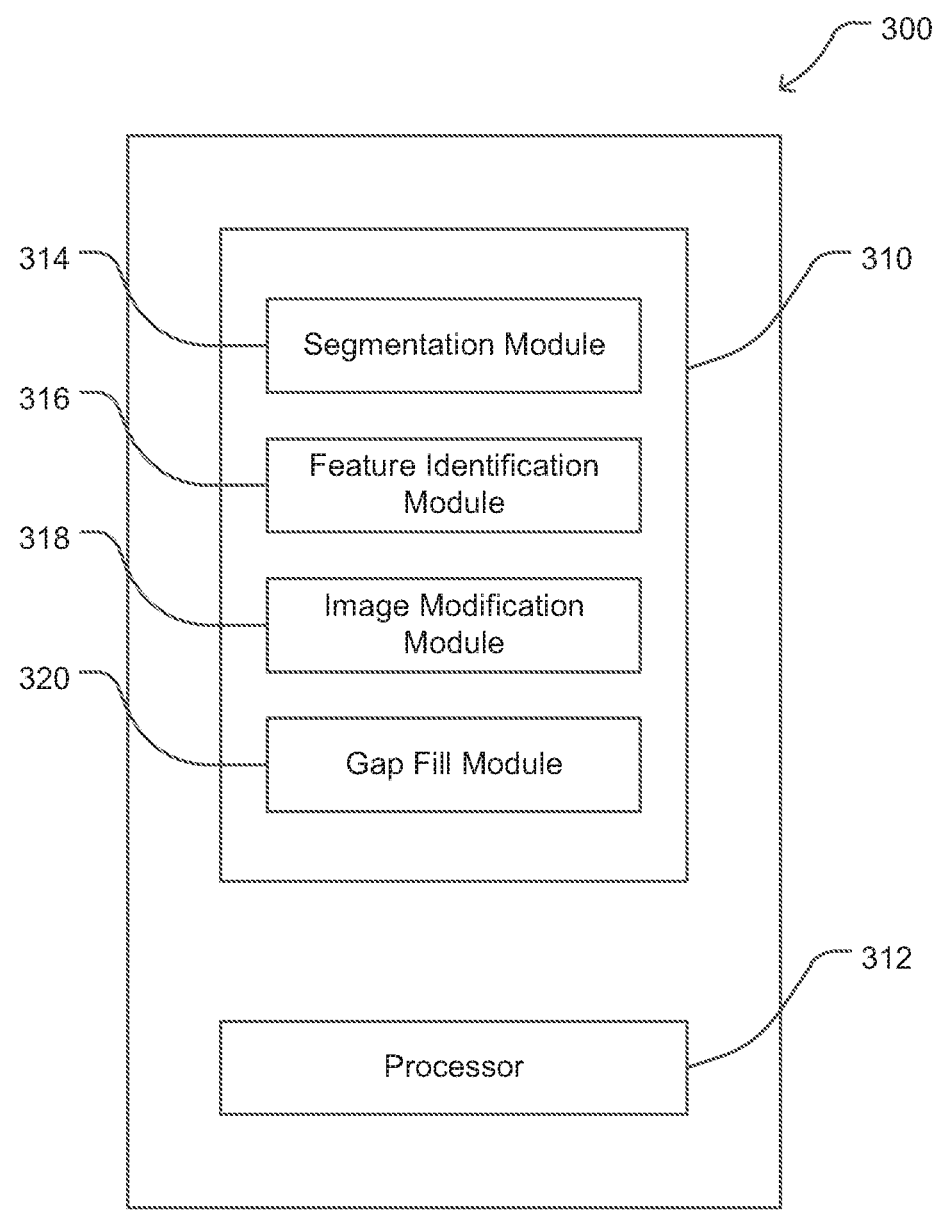
FIG. 3 is a block diagram illustrating components of a processing circuit of an ultrasound system according to an illustrative embodiment.

Referring now to FIG. 3, an embodiment of a processing circuit 300 of an ultrasound system (e.g., ultrasound system 100) is illustrated. The processing circuit 300 includes a memory 310 and a processor 312. The processing circuit 300 can be similar to and perform similar functions as the processing circuit 210 described herein with reference to FIG. 2. For example, the memory 310 can be similar to the memory 212, and the processor 312 can be similar to the processor 214. As described herein with reference to FIG. 3, the processing circuit 300 (and particularly, memory 310 thereof) can include various electronic modules (e.g., segmentation module 314, etc.), configured to execute various functions performed by an ultrasound system; in various embodiments, the processing circuit 300 can be organized in various ways for determining how functions are executed. The modules can be configured to share responsibilities by sending instructions to each other to execute algorithms and other functions, and receiving outputs generated by the module receiving the instructions. While FIG. 3 (and FIG. 4) illustrate an example arrangement of modules of the memory 310 and processes executed by the modules, it will be appreciated that the sequence of process execution may be various according to various implementations; for example, the segmentation module 314 or feature identification module 316 can be executed before or after gain processing or dynamic range processing is executed.

In some embodiments, the processing circuit 300 is configured to execute morphological or spatial processing of ultrasound information, such as ultrasound data samples or ultrasound images. The processing circuit 300 can receive ultrasound data samples from an ultrasound transducer (e.g., an ultrasound transducer similar or identical to ultrasound transducer assembly 102). The ultrasound data sample can correspond to or represent ultrasound information such as features of blood flow or vasculature of the patient. The ultrasound data sample can be raw data from the ultrasound transducer. For example, the ultrasound data sample can be an analog radio frequency signal outputted by the ultrasound transducer, or a digital data signal resulting from processing of the analog radio frequency signal by an analog-to-digital converter. The ultrasound data sample can represent a velocity of blood at a single point or within a region in space in the patient. The ultrasound data sample can represent a vascular feature of the patient, such as a wall of an artery or a vein.

The ultrasound data sample can correspond to individual points of ultrasound information (e.g., a single point corresponding to amplitude, frequency, time, and/or position information; a single point corresponding to a velocity and time pair), or can be organized into segments corresponding to durations of time, such as durations of time corresponding to a heart cycle of a patient (e.g., sequences of points corresponding amplitude, frequency, time, and/or position information; sequences of points corresponding to velocities paired with times of a heart cycle of a patient). For example, an ultrasound data sample can include a sequence of data point pairs (e.g., raw data) of [frequency, time] corresponding to a heart cycle; or, if a Doppler equation algorithm has been executed to process the raw data, the ultrasound data sample can include a sequence of data point pairs of [velocity, time] corresponding to a heart cycle, or any other sequence of data point pairs corresponding to a Doppler spectrum based on the ultrasound information. In some embodiments, rather than a first plurality of ultrasound data samples, a single first ultrasound data sample is used for possible inclusion when modifying the current ultrasound data sample. This can be beneficial in systems and patient conditions where blood flow is relatively dynamic, by emphasizing only the current and most recent ultrasound data sample while still providing the benefit of persisting signal information from the prior ultrasound data sample. The processing circuit 300 may be configured to execute a Doppler equation algorithm to determine velocity information (e.g., velocity as a function of time at a particular position).

In some embodiments, the processing circuit 300 includes a segmentation module 314. The segmentation module 314 is configured to segment ultrasound information, such as ultrasound data samples or an image generated by the processing circuit 300 from ultrasound data samples or spectra. The information for segmentation can be arranged as an array or matrix (e.g., a matrix of pixels) associating spatial positions of the anatomy of patient with brightness values, the brightness values corresponding to the output of the ultrasound transducer. While the segmentation module 314 is described herein as executing segmentation processes on binary images, it will be appreciated that the processing circuit 300 may execute other morphological processing algorithms to obtain the location of vascular features based on ultrasound information, including morphological processing algorithms that may be executed on grayscale images.

In some embodiments, the processing circuit 300 is configured to provide the information for segmentation by the segmentation module 314 based on an expected location of anatomical features or a region of interest. For example, the processing circuit 300 can receive a user input indicating a selection of an expected location of vessel walls, such as locations of proximal and/or distal carotid artery walls. The processing circuit 300 can receive an indication of an imaging depth, such as an indication received from the ultrasound transducer or determined based on imaging data associated with the ultrasound transducer, and adjust the ultrasound information based on the imaging depth.

The processing circuit 300 can be configured to pre-process the information for segmentation by the segmentation module 314. For example, the processing circuit 300 can execute at least one of a spatial filter algorithm or an edge enhancement algorithm on the ultrasound information, such as to enhance a portion of the ultrasound information corresponding to the indication of an expected location of vessel walls. The at least one of the spatial filter algorithm or edge enhancement algorithm can be executed based on brightness information, such as by determining an expected boundary of the vessel walls based on the brightness information. The at least one of the spatial filter algorithm or edge enhancement algorithm can be executed simultaneously or separately for each of a proximal wall and a distal wall of a vessel, such as the carotid artery.

The segmentation module 314 can segment the ultrasound information into a binary image including at least one first region and at least one second region. The binary image can include one or more boundaries defining the at least one first region and the at least one second region. In some embodiments, the segmentation module 314 is configured to segment the ultrasound information based on a brightness threshold. The brightness threshold can be a predetermined threshold. The brightness threshold can be selected or predetermined based on an anatomy of the patient. The brightness threshold can be set to distinguish regions that correspond to vascular walls from regions that correspond to blood. For example, where bright regions are generally associated with vascular walls and dark regions are generally associated with blood, the brightness threshold can be set to a value less than an expected brightness or expected minimum brightness of vascular walls, or to a value greater than an expected brightness or expected maximum brightness of blood. In some embodiments, segmenting the ultrasound information includes comparing brightness of each pixel to the brightness threshold, assigning a first value (e.g., 1) to pixels having a brightness greater than the brightness threshold, and assigning a second value (e.g., 0) to pixels having a brightness less than or equal to the brightness threshold. In some embodiments, the segmentation module 314 is configured to segment the ultrasound information into a grayscale image (e.g., an image having more than one brightness level, as compared to binary image having two brightness levels).

The segmentation module 314 can segment the ultrasound information such that the at least one first region corresponds to one or more regions having a brightness greater than the brightness threshold and the at least one second region corresponds to one or more regions having a brightness less than or equal to the brightness threshold. In some embodiments, the segmentation module 314 is configured to identify the boundary between the at least one first region and the at least one second region based on a difference in brightness between the at least one first region and the at least one second region. For example, the segmentation module 314 can sort or categorize the first region(s) and second region(s) based on brightness values associated with the corresponding regions in order to generate the boundary. The segmentation module 314 can calculate a brightness gradient between regions to generate the boundary (e.g., a relatively large gradient may indicate the boundary between relatively bright vascular wall features and relatively dark blood flow). The segmentation module 312 can generate the boundary to be between relatively bright regions (e.g., regions having brightness greater than the brightness threshold) and relatively dark regions (e.g., regions having brightness less than the brightness threshold).

In some embodiments, the segmentation module 314 is configured to execute an image dilation algorithm, such as to join some disjointed regions and remove small regions of the binary image. Executing the image dilation algorithm can include generating a structure element (e.g., a kernel), calculating a union of the structuring element and the binary image, and modifying the binary image based on the union. The structuring element may be a matrix of coordinate points smaller in dimension than the binary image (e.g., if the binary image is a m by n matrix of pixels, the structuring element may be a k by l matrix of pixels, where k is less than m and l is less than n; the values for each of the pixels of the structuring element may be set to 1 where bright pixels in the binary image are also set to 1). The structuring element can be generated based on at least one of anatomical information or a imaging dimension associated with the binary image. For example, based on the at least one of the anatomical information or imaging dimension, the segmentation module 314 can determine an expected size (in pixels) of the vascular feature (e.g., a lumen-intima wall) and generate the structuring element to be less than the size of the vascular feature, such that the structuring element effectively dilates the binary image without obscuring the underlying vascular feature.

In some embodiments, the processing circuit 300 includes a feature identification module 316. The feature identification module 316 is configured to identify or locate features of the patient in the binary image. The feature identification module 316 can identify vascular features such as veins, arteries, and walls thereof. The feature identification module 316 can identify the lumen, intima, media, and/or adventitia, including interfaces of these vascular features.

The feature identification module 316 can obtain a location of a vascular feature of a binary image (e.g., the image segmented or generated by the segmentation module 314) based on the boundary between the at least one first region and the at least one second region. For example, the feature identification module 316 can determine the boundary to be a boundary between a lumen and an intima portion of a vessel wall (e.g., a lumen-intima line). The feature identification module 316 can associate the boundary with a vascular feature based on an expected brightness for the vascular feature or an expected thickness for the vascular feature.

In some embodiments, the feature identification module 316 is configured to obtain a preliminary location of a vascular feature, and then obtain a subsequent or final location which may be used for modifying the binary image. The preliminary location may be obtained based on the boundary. For example, the feature identification module 316 can detect one or more lines (e.g., straight lines, curves) in the binary image which may be close in space to the boundary. The one or more lines may coincide with the boundary, or may be calculated to be lines which minimize a distance from the boundary. In some such embodiments, obtaining the preliminary locations provides an initial or coarse search for the vascular feature, which may be more precisely updated.

The feature identification module 316 can identify the subsequent location based on at least one of a distance threshold or a brightness threshold. The subsequent location may be used as a more accurate location for the vascular feature.

The distance threshold may correspond to the vascular feature to be located. For example, the distance threshold may correspond to an expected intima media thickness. As compared to existing ultrasound systems, which estimate or calculate an unknown intima media thickness in order to assess whether vessel walls are diseased, the feature identification module 316 can use a known or expected intima media thickness value to more precisely define the locations of the lumen (carrying blood flow) and vessel walls, including the intima, media, and adventitia portions of vessel walls. For example, if preliminary locations of a lumen-intima line and a media-adventitia line indicate an intima media thickness that is less than (or greater than) a known or expected intima media thickness value, the location of the lumen-intima line and/or the media-adventitia line may be adjusted to more closely correspond to the expected intima media thickness value. In some embodiments, the feature identification module can 316 can be configured to calculate previously unknown parameters such as intima media thickness or wall diameter; the feature identification module 316 can more accurately and/or precisely calculate such parameters, as compared to existing systems, based on the improved methods described herein for obtaining locations of vascular features such as lumen-intima and media-adventitia lines.

In some embodiments, both a distance threshold and a brightness threshold may be used to update the preliminary location to update the location of the vascular features. The distance threshold may establish a maximum distance from the preliminary location by which the preliminary location may be updated, and the brightness threshold may estimate target values or ranges of values for brightness associated with the vascular features. The brightness threshold may correspond to a known value or range of values for brightness of the intima, media, and/or adventitia.

In some embodiments, the feature identification module 316 is configured to obtain the location of vascular features additionally or alternatively to receiving a binary image segmented by the segmentation module 314. For example, the feature identification module 316 can execute a curve fitting algorithm, such as a quadratic or other polynomial curve fitting algorithm, to data points associated with vascular features such as lumen-intima lines or media-adventitia lines. If the data points have not been previously segmented or otherwise processed by the segmentation module 314, the feature identification module 316 can identify the data points for curve fitting based on brightness values in the binary image.

The feature identification module 316 can execute a clustering algorithm to obtain the location of vascular features. For example, the feature identification module 316 can execute a K-means algorithm to cluster regions based on brightness. The K-means algorithm may be executed to obtain an initial or preliminary location of vascular features such as lumen-intima lines or media-adventitia lines, which may later be refined to more obtain more precise and/or accurate locations for these features. The K-means algorithm may be used to cluster regions based on brightness and determine one or more boundaries between clusters based on brightness values or brightness thresholds. In some embodiments, the feature identification module 316 can be configured to execute the clustering algorithm automatically (e.g., without receiving a user input indicating a location of the vascular feature to initialize the clustering algorithm). In some embodiments, the feature identification module 316 is configured to execute a dynamic programming algorithm to obtain a subsequent or final location of vascular features based on the initial or preliminary location. For example, the dynamic programming algorithm can be executed to refine, improve, or optimize the location of the vascular feature based on brightness data. The dynamic programming algorithm can be executed to identify an optimal boundary separating relatively bright clusters from relatively dark clusters as obtained by the K-means algorithm, thus refining the location of the vascular feature.

In some embodiments, the feature identification module 316 is configured to execute a curve detection algorithm for enhancing the detection of vascular features or other anatomical features. For example, the curve detection algorithm can be executed to detect elliptical or circular features. The elliptical or circular features may be associated with anatomical features corresponding to clinical applications such as cardiology or OB/GYN applications. For example, the feature identification module 316 can be configured to detect curves and compare the detected curves to a database of known anatomical features to identify the associated anatomical feature and/or refine the detected curve based on an expected anatomical feature. The feature identification module 316 can be configured to output the binary image to include an indication of the anatomical features detected based on executing the curve detection algorithm, such as for when the image is displayed.

In some embodiments, the processing circuit 300 includes an image modification module 318 configured to modify the binary image based on locations of vascular features. The image modification module 318 can modify the binary image by changing parameters of the image such as brightness or color values associated with spatial positions (e.g., pixels) of the binary image. The image modification module 318 can use the locations of vascular features to more accurately differentiate blood flow within vessels from the vessel walls.

The image modification module 318 can be configured to modify the binary image by decreasing a brightness associated with the lumen-intima media line. Decreasing the brightness may include setting the brightness to a zero value or close to a zero value, such as to remove the lumen-intima media line. This may facilitate more clearly defining the boundary between the vessel walls on the intima side of the lumen-intima media line and the lumen. For example, in Color Doppler imaging modes, by decreasing the brightness associated with the lumen-intima media line, color regions beyond these lines (e.g., color regions extending into the lumen) may be removed, which can improve the displayed image by reducing bleed or overflow of color. The image modification module 318 also modify the binary image by removing color from the vascular feature (e.g., removing color from a vessel wall region based on obtaining the location of the vessel wall region).

The image modification module 318 can modify the binary image based on a predetermined size dimension associated with a vascular feature. The predetermined size dimension may be a thickness of the vessel wall. For example, the predetermined size dimension may be an intima-media thickness value. The image modification module 318 can modify how a vessel wall is displayed (e.g., decreasing brightness or removing color from edges of the vessel wall) based on the predetermined size dimension. For example, the image modification module 318 can reduce a brightness or remove a color of a portion of the vessel wall, such as an edge or boundary adjacent to blood flow, so that an apparent intima-media thickness of the vessel wall in the binary image corresponds to a known or expected intima-media thickness value.

In some embodiments, the image modification module 318 is configured to modify the binary image based on the obtained location of vascular features to reduce clutter. For example, B-mode data associated with lumen-intima line locations can be suppressed (e.g., decreased in intensity or brightness) to reduce clutter from the vascular features that might otherwise extend into the displayed blood flowing through the lumen.

The image modification module 318 can modify the binary image based on whether a vascular feature is associated with an artery or a vein. For example, venous regions may typically be devoid of lumen-intima lines. The processing circuit 300 can determine a region to be venous by identifying regions associated with vessel walls (e.g., based on detecting a difference in brightness across regions), and determining that a location for a lumen-intima line has not been obtained in the vessel wall region. Based on determining that a region is venous, the image modification module 318 can modify at least one of a brightness or a color associated with the vascular feature.

In some embodiments, such as when generating an image for color Doppler imaging modes, the image modification module 318 can adapt a color Doppler parameter based on determining whether a vascular feature corresponds to an arterial region or a venous region. For example, the image modification module 318 can modify at least one of a wall filter or a flow state filter based on whether the vascular feature is associated with a venous region or an arterial region.

The image modification module 318 can execute a wall filter configured to identify and remove low-frequency components in ultrasound information detected by the ultrasound transducer assembly 102, such as by applying a high pass filter to the ultrasound information. The high pass filter can be calibrated based on stored information regarding typical frequencies detected for blood flow, as compared to typical frequencies detected for blood vessel walls The high pass filter can be calibrated dynamically and/or in response to user input, such as user input indicating feedback from a user describing whether a displayed spectrum of ultrasound data includes information representative of blood vessel walls. Based on determining that a vascular feature corresponds to an arterial region or a venous region, the image modification module 318 can recalibrate the wall filter (e.g., modify a filter frequency threshold) to more accurately differentiate blood flow from a vessel wall associated with the vascular feature.

The image modification module 318 can execute a flow state filter configured to modify parameters for displaying blood flow. For example, the flow state filter can modify parameters for displaying blood flow based on a flow rate or velocity of the blood flow. The image modification module 318 can modify the flow state filter based on whether a vascular feature corresponds to an arterial region or a venous region. For example, based on determining that the vascular feature corresponds to an arterial region (or a venous region), the image modification module 316 can modify an expected velocity, expected flow rate, or range of expected velocities (or expected flow rates) used by the flow state filter.

In some embodiments, a first vascular feature is associated with a first wall of a blood vessel (e.g., a wall proximal to the ultrasound transducer), and a second vascular feature is associated with a second wall of the blood vessel (e.g., a wall distal from the ultrasound transducer). The feature identification module 316 can be configured to obtain the locations of at least one of the first vascular feature or the second vascular feature and the image modification module 318 can be configured to modify the image based on at least one of the first location or the second location.

The image modification module 318 can be configured to modify the image based on user input. For example, the image modification module 318 can receive user input indicating instructions to modify at least one of a gain or a dynamic range of the displayed image. The image modification module 318 can modify a brightness of pixels of the image for display based on the user input.

In some embodiments, the processing circuit 300 is configured to receive a plurality of ultrasound data samples from the ultrasound transducer. The processing circuit 300 can continuously modify a plurality of images to be displayed based on obtaining locations of vascular features. For example, the processing circuit 300 can obtain the location of vascular features such as at least one of the media-adventitia line or the lumen-intima line for a first ultrasound data sample. For a second ultrasound data sample (e.g., a subsequent ultrasound data sample), the processing circuit 300 can use the location of the vascular features as an initial or preliminary location for obtaining corresponding locations in the second ultrasound data sample. In some such embodiments, the processing circuit 300 can obtain the location of at least one of the media-adventitia line or the lumen-intima line in a first frame (e.g., a frame generated based on ultrasound information), and adapt the location of the at least one of the media-adventitia line or the lumen-intima line in a second frame.

The processing circuit 300 can initialize an image mode for displaying the modified binary image based on identifying vascular features or obtaining locations of vascular features. For example, the processing circuit 300 can initialize parameters such as flow state parameters, colors associated with blood flow or with vessel walls, brightness values associated with blood flow or with vessel walls, or other ultrasound display parameters so that the image displayed more accurately and precisely illustrates the underlying anatomy of the patient. The processing circuit 300 can initialize color Doppler region of interest size, color Doppler region of interest location, color Doppler pulse repetition frequency, color Doppler steering, pulsed wave Doppler gate size, pulsed wave Doppler gate position, pulsed wave Doppler steer angle, or other imaging parameters.

The processing circuit 300 can automatically and/or dynamically execute determination of key ultrasound parameters based on the obtained locations of vascular features. For example, the processing circuit 300 can determine the intima-media thickness, wall diameter, and/or a selected imaging view based on the obtained locations of vascular features.

In some embodiments, the processing circuit 300 generates improved ultrasound image information for display based on modified binary image because the modified binary image more accurately and/or more precisely differentiates blood flow from vascular features such as vessel walls, reducing bleed or color overflow and reducing clutter in the blood flow.

Figure 4:
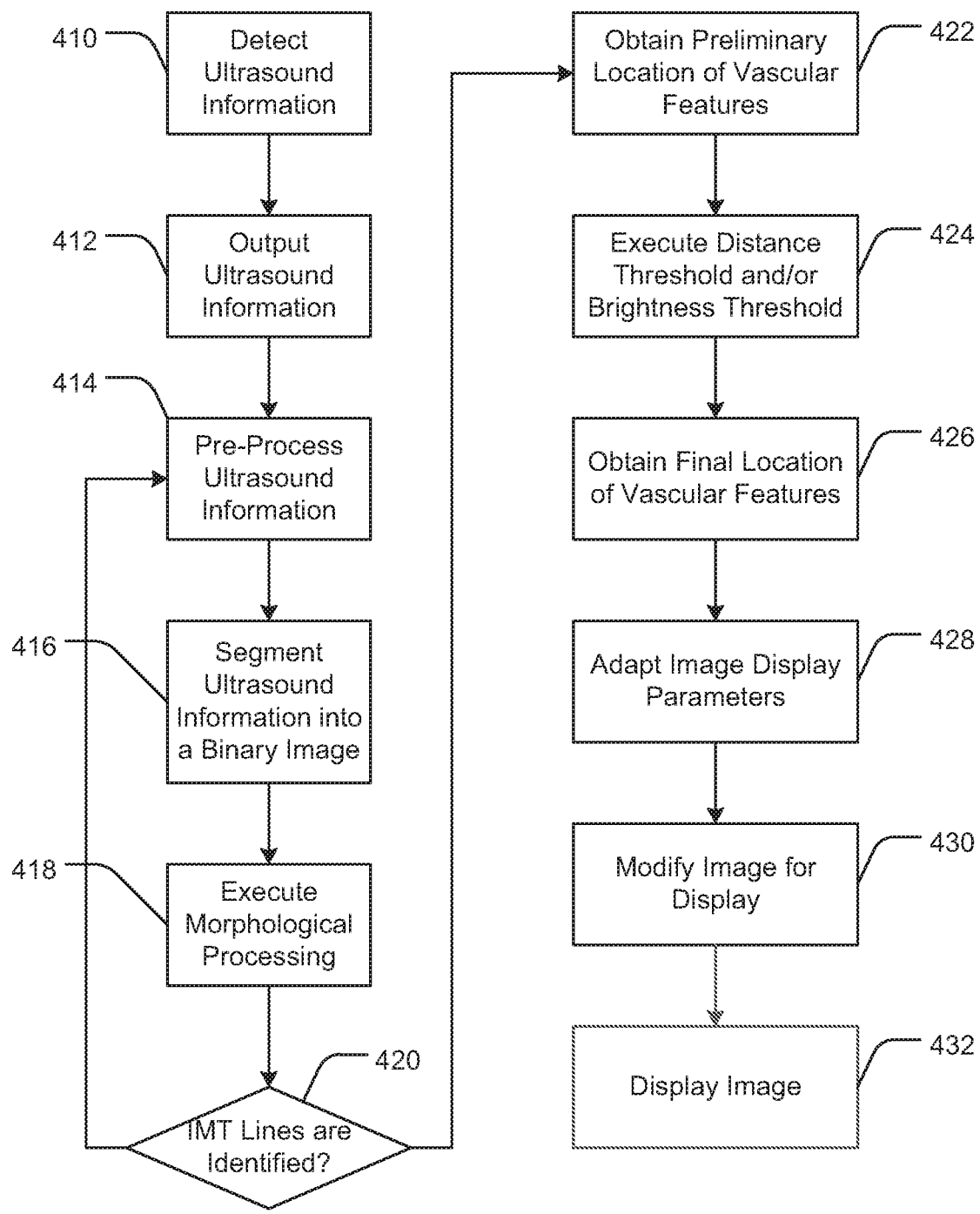
FIG. 4 is a flow chart of a method of adaptively enhancing vascular imaging, according an embodiment of the present disclosure.

Referring now to FIG. 4, a method 400 for adaptive enhancement of vascular imaging is illustrated. The method 400 can be implemented by an ultrasound system, such as ultrasound system 100, an ultrasound system including processing circuit 300, etc. The method 400 can be performed for displaying an ultrasound spectrum or image to a user performing an ultrasound diagnostic procedure.

At 410, ultrasound information is detected. For example, an ultrasound transducer probe can be positioned adjacent to the patient to detect ultrasound information from the patient.

At 412, the ultrasound information is outputted as an ultrasound data sample. The ultrasound transducer probe can output the ultrasound information as frequency information. In some embodiments, the ultrasound transducer probe can be configured to process the frequency information into velocity information as a function of time, and output the ultrasound data sample as the velocity information as a function of time.

At 414, ultrasound information is pre-processed. Pre-processing the ultrasound information can include detecting a region of interest (e.g., automatically based on expected anatomical features; in response to user input indicating a region of interest). Pre-processing the ultrasound information can include executing gain processing or dynamic range processing, which may be performed automatically or based on user input. Pre-processing the ultrasound information can include executing at least one of a spatial filter algorithm or an edge enhancement algorithm, such as to differentiate vessel walls from blood flow.

At 416, the ultrasound information is segmented into a binary image. The binary image can include at least one first region and at least one second region. The ultrasound information can be segmented based on brightness or a brightness threshold.

At 418, morphological processing is executed. The morphological processing can include executing an image dilation algorithm on the binary image, such as to join some disjointed regions and remove small regions of the binary image. The morphological processing can include identifying one or more lines corresponding to bright wall boundaries.

At 420, it is determined whether intima-media thicknesses or lines have been or can be identified. For example, if both a lumen-intima line and a media-adventitia line have been obtained or can be obtained, then the intima-media thickness may be identified. If the intima-media thickness has not been identified, then further processing, including segmentation and morphological processing, may be executed.

At 422, if intima-media thickness lines have been identified, then preliminary locations of vascular features, such as lumen-intima lines and media-adventitia lines for proximal and distal vessel walls, are obtained. Obtain preliminary locations of vascular features can include determining boundaries between bright and dark regions in the binary image to correspond to particular anatomies (e.g., based on expected dimensions of vascular features).

At 424, at least one of a distance threshold or a brightness threshold can be executed. The distance threshold may be used to define a region within a location of the vascular feature can be refined or optimized, and the brightness threshold can be used to filter pixels corresponding to expected vascular features from pixels not corresponding to expected vascular features. At 426, final locations of vascular features are obtained. The final locations may be obtained based on the execute of the distance threshold and/or the brightness threshold.

At 428, image display parameters are adapted. For example, parameters associated with an imaging mode to be used to display the image, or associated with a flow state, may be adapted for a current frame and for subsequent frames.

At 430, the image is modified for display. In B-mode imaging, clutter from vessel walls may be suppressed in the portion of the image corresponding to blood flow. Contrast can be enhanced between vessel walls and blood flow. Arteries and veins can be differentiated (e.g., based on color or brightness modifications). In color Doppler imaging, color bleed from vessel wall regions to blood flow regions can be reduced, such as by removing color from regions determined to correspond to blood flow based on obtaining the location of vascular features. At 432, the image is displayed.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system, comprising:
    an ultrasound transducer configured to detect ultrasound information regarding a patient and output the ultrasound information as an ultrasound data sample;
    a processing circuit configured to:
    segment the ultrasound data sample into a binary image including at least one first region and at least one second region;

obtain a first location of a first vascular feature of the binary image based on a boundary between the at least one first region and the at least one second region; and modify the binary image based on the first location of the first vascular feature; and a display configured to display the modified image, wherein the processing circuit is further configured to obtain a second location of a second vascular feature of the binary image based on: identifying a second preliminary location based on the boundary between the at least one first region and the at least one second region; and identifying the second location based on a distance threshold indicating a maximum distance from the second preliminary location and a brightness threshold indicating a minimum brightness associated with the second vascular feature;

wherein the first vascular feature includes a media-adventitia line and the second vascular feature includes a lumen-intima line; and the processing circuit is configured to modify the binary image by decreasing a brightness of pixels of the binary image associated with the second vascular feature.

2. The system of claim 1, wherein the processing circuit is configured to segment the ultrasound data sample based on a brightness threshold such that the at least one first region corresponds to one or more regions having a brightness greater than the brightness threshold and the at least one second region corresponds to one or more regions having a brightness less than or equal to the brightness threshold.

3. The system of claim 1, wherein the processing circuit is configured to obtain the first location based on dilating the binary image, wherein dilating the binary image includes generating a structuring element, calculating a union of the structuring element and the binary image, and modifying the binary image based on the union.

4. The system of claim 1, wherein the processing circuit is configured to identify the boundary between the at least one first region and the at least one second region based on a difference in brightness between the at least one first region and the at least one second region.

5. The system of claim 1, wherein the processing circuit is configured to obtain the first location of the first vascular feature based on:

identifying a first preliminary location based on the boundary; and identifying the first location based on a distance threshold indicating a maximum distance from the first preliminary location and a brightness threshold indicating a minimum brightness associated with the first vascular feature.

6. The system of claim 1, wherein the first vascular feature is associated with a proximal wall of a blood vessel, and the processing circuit is further configured to obtain a second location of a second vascular feature associated with a distal wall of the blood vessel and modify the binary image based on the second location.

7. The system of claim 1, wherein the processing circuit is further configured to receive a plurality of ultrasound data samples from the ultrasound transducer and continuously modify a plurality of images to be displayed based on obtaining the first location of the first vascular feature.

8. The system of claim 1, wherein the processing circuit is configured to modify the binary image by modifying at least one of a brightness or a color associated with the first vascular feature based on whether the first vascular feature is associated with a venous region or an arterial region.

9. The system of claim 1, wherein the display is configured to display the modified image in a color Doppler mode, and the processing circuit is configured to modify the image based on applying at least one of a wall filter or a flow state filter based on whether the first vascular feature is associated with a venous region or an arterial region.

10. The system of claim 1, wherein the display is configured to display the modified image in a color Doppler mode, and the processing circuit is configured to differentiate a blood flow region from a vessel wall region based on the first location of the first vascular feature and modify the binary image by removing color from the vessel wall region.

11. The system of claim 1, wherein the processing circuit is further configured to modify the binary image based on a predetermined size dimension associated with the first vascular feature.

12. The system of claim 1, wherein the processing circuit is further configured to initialize an image mode for displaying the modified image based on the first vascular feature.

13. A computer-implemented method, comprising:

receiving an ultrasound data sample associated with ultrasound information regarding a patient;

segmenting the ultrasound data sample into a binary image including at least one first region and at least one second region;

obtaining a first location of a first vascular feature of the binary image based on a boundary between the at least one first region and the at least one second region;

modifying the binary image based on the first location of the first vascular feature; and displaying the modified image, wherein the method further comprises:

obtaining a second location of a second vascular feature of the binary image based on:

identifying a second preliminary location based on the boundary between the at least one first region and the at least one second region;

identifying the second location based on a distance threshold indicating a maximum distance from the second preliminary location and a brightness threshold indicating a minimum brightness associated with the second vascular feature, wherein the first vascular feature includes a media-adventitia line and the second vascular feature includes a lumen-intima line; and modifying the binary image by decreasing a brightness of pixels of the binary image associated with the second vascular feature.

14. The method of claim 13, wherein segmenting the ultrasound data sample includes segmenting the ultrasound data sample such that the at least one first region corresponds to one or more regions having a brightness greater than the brightness threshold and the at least one second region corresponds to one or more regions having a brightness less than or equal to the brightness threshold.

15. The method of claim 13, further comprising identifying the boundary between the at least one first region and the at least one second region based on a difference in brightness between the at least one first region and the at least one second region.

16. The method of claim 13, wherein obtaining the first location of the first vascular feature includes:

identifying a first preliminary location based on the boundary; and identifying the first location based on a distance threshold indicating a maximum distance from the first preliminary location and a brightness threshold indicating a minimum brightness associated with the first vascular feature.

17. The method of claim 13, further comprising:
identifying a second preliminary location of a second vascular feature of the binary image based on the boundary between the at least one first region and the at least one second region; and
identifying a second location of the second vascular feature based on a distance threshold indicating a maximum distance from the second preliminary location and a brightness threshold indicating a minimum brightness associated with the second vascular feature;
wherein the first vascular feature includes a media-adventitia line and the second vascular feature includes a lumen-intima line.

18. A system, comprising:
a processing circuit configured to:
receive an ultrasound data sample from an ultrasound transducer, the ultrasound data sample representing an anatomy of a patient;
segment the ultrasound data sample into a binary image including at least one first region and at least one second region;
obtain a first location of a first vascular feature of the binary image based on a boundary between the at least one first region and the at least one second region; and
modify the binary image based on the first location of the first vascular feature; and
display the modified image on a display,
wherein the processing circuit is further configured to obtain a second location of a second vascular feature of the binary image based on: identifying a second preliminary location based on the boundary between the at least one first region and the at least one second region; and
identifying the second location based on a distance threshold indicating a maximum distance from the second preliminary location and a brightness threshold indicating a minimum brightness associated with the second vascular feature;
wherein the first vascular feature includes a media-adventitia line and the second vascular feature includes a lumen-intima line; and
the processing circuit is configured to modify the binary image by decreasing a brightness of pixels of the binary image associated with the second vascular feature.

* * * * *